US012642578B2

(12) United States Patent
Allen, IV et al.

(10) Patent No.: US 12,642,578 B2
(45) Date of Patent: Jun. 2, 2026

(54) THERMAL CUTTING ELEMENTS AND ELECTROSURGICAL INSTRUMENTS INCLUDING THERMAL CUTTING ELEMENTS

(71) Applicant: Covidien LP, Mansfield, MA (US)

(72) Inventors: James D. Allen, IV, Broomfield, CO (US); William E. Robinson, Boulder, CO (US); Daniel A. Joseph, Golden, CO (US); John A Hammerland, III, Arvada, CO (US); Kenneth E. Netzel, Loveland, CO (US)

(73) Assignee: Covidien LP, Mansfield, MA (US)

( * ) Notice: Subject to any disclaimer, the term of this patent is extended or adjusted under 35 U.S.C. 154(b) by 512 days.

(21) Appl. No.: 18/032,997

(22) PCT Filed: Sep. 21, 2021

(86) PCT No.: PCT/US2021/051192
§ 371 (c)(1),
(2) Date: Apr. 20, 2023

(87) PCT Pub. No.: WO2022/086656
PCT Pub. Date: Apr. 28, 2022

(65) Prior Publication Data
US 2023/0380885 A1      Nov. 30, 2023

Related U.S. Application Data

(60) Provisional application No. 63/093,936, filed on Oct. 20, 2020.

(51) Int. Cl.
*A61B 18/14*       (2006.01)
*A61B 18/00*       (2006.01)

(52) U.S. Cl.
CPC ................... *A61B 18/1442* (2013.01); *A61B 2018/00077* (2013.01); *A61B 2018/00601* (2013.01);
(Continued)

(58) Field of Classification Search
CPC ............ A61B 18/1445; A61B 18/1442; A61B 2018/1452
See application file for complete search history.

(56) References Cited

U.S. PATENT DOCUMENTS

| | | | |
|---|---|---|---|
| 2,068,721 A | 1/1937 | Frederick | |
| 4,091,813 A | 5/1978 | Shaw et al. | |

(Continued)

FOREIGN PATENT DOCUMENTS

| | | |
|---|---|---|
| EP | 2754403 A2 | 7/2014 |
| WO | 2008008457 A2 | 1/2008 |

OTHER PUBLICATIONS

Gnedenkov et al., "Magnesium fabricated using additive technology: Specificity of corrosion and protection", Journal of Alloys and Compounds, Elsevier, vol. 808, Jul. 29, 2019, XP085792710.
(Continued)

*Primary Examiner* — Linda C Dvorak
*Assistant Examiner* — Ryan T Clark

(57)      ABSTRACT

An end effector assembly for an electrosurgical instrument includes a pair of opposing jaw members each having a jaw housing supporting an electrically conductive tissue engaging surface thereon. The electrically conductive tissue engaging surfaces are disposed in opposition relative to one another. The jaw members are movable relative to one another to grasp tissue therebetween and are connect to an electrosurgical energy source. A thermal cutting element is disposed in one of the electrically conductive tissue engaging surfaces and is independently activatable relative to the electrically conductive tissue engaging surfaces. The ther-
(Continued)

mal cutting element is exposed along the length of the electrically conductive tissue engaging surface and includes an exposed distal end extending through a distal end of the jaw housing. The thermal cutting element includes a scallop defined proximal to the exposed distal end thereof configured to facilitate tissue scoring upon movement and activation thereof.

18 Claims, 5 Drawing Sheets

(52) U.S. Cl.
CPC ............... *A61B 2018/00779* (2013.01); *A61B 2018/00791* (2013.01); *A61B 2018/1452* (2013.01)

(56) References Cited

U.S. PATENT DOCUMENTS

| | | | |
|---|---|---|---|
| 5,389,098 A | 2/1995 | Tsuruta et al. | |
| 5,403,312 A | 4/1995 | Yates et al. | |
| 5,465,895 A | 11/1995 | Knodel et al. | |
| 5,810,811 A | 9/1998 | Yates et al. | |
| 5,827,271 A | 10/1998 | Buysse et al. | |
| 5,833,690 A | 11/1998 | Yates et al. | |
| 5,876,401 A | 3/1999 | Schulze et al. | |
| 5,911,719 A | 6/1999 | Eggers | |
| 6,024,741 A | 2/2000 | Williamson, IV et al. | |
| 6,086,586 A | 7/2000 | Hooven | |
| 6,273,887 B1 | 8/2001 | Yamauchi et al. | |
| 6,402,747 B1 | 6/2002 | Lindemann et al. | |
| 6,602,252 B2 | 8/2003 | Mollenauer | |
| 6,736,813 B2 | 5/2004 | Yamauchi et al. | |
| 6,776,780 B2 | 8/2004 | Mulier et al. | |
| 6,802,843 B2 | 10/2004 | Truckai et al. | |
| 6,808,525 B2 | 10/2004 | Latterell et al. | |
| 6,821,273 B2 | 11/2004 | Mollenauer | |
| 6,860,880 B2 | 3/2005 | Treat et al. | |
| 6,899,710 B2 | 5/2005 | Hooven | |
| 6,929,641 B2 | 8/2005 | Goble et al. | |
| 6,953,461 B2 | 10/2005 | McClurken et al. | |
| 7,011,656 B2 | 3/2006 | McGaffigan et al. | |
| 7,033,356 B2 | 4/2006 | Atterell et al. | |
| 7,070,597 B2 | 7/2006 | Truckai et al. | |
| 7,083,619 B2 | 8/2006 | Truckai et al. | |
| 7,112,201 B2 | 9/2006 | Truckai et al. | |
| 7,125,409 B2 | 10/2006 | Truckai et al. | |
| 7,147,637 B2 | 12/2006 | Goble | |
| 7,169,146 B2 | 1/2007 | Truckai et al. | |
| 7,204,835 B2 | 4/2007 | Latterell et al. | |
| 7,270,664 B2 | 9/2007 | Johnson et al. | |
| 7,276,068 B2 | 10/2007 | Johnson et al. | |
| 7,326,202 B2 | 2/2008 | McGaffigan | |
| 7,329,255 B2 | 2/2008 | McGaffigan | |
| 7,331,972 B1 | 2/2008 | Cox | |
| 7,354,440 B2 | 4/2008 | Truckai et al. | |
| 7,357,802 B2 | 4/2008 | Palanker et al. | |
| 7,364,577 B2 | 4/2008 | Wham et al. | |
| 7,396,356 B2 | 7/2008 | Mollenauer | |
| 7,419,490 B2 | 9/2008 | Falkenstein et al. | |
| 7,686,827 B2 | 3/2010 | Hushka | |
| 7,815,641 B2 | 10/2010 | Dodde et al. | |
| 7,931,649 B2 | 4/2011 | Couture et al. | |
| 8,034,051 B2 | 10/2011 | Martin et al. | |
| 8,162,940 B2 | 4/2012 | Johnson et al. | |
| 8,187,273 B2 | 5/2012 | Kerr et al. | |
| 8,197,472 B2 | 6/2012 | Lau et al. | |
| 8,226,649 B2 | 7/2012 | Falkenstein et al. | |
| 8,292,879 B2 | 10/2012 | Manwaring et al. | |
| 8,303,585 B2 | 11/2012 | Mollenauer | |
| 8,372,066 B2 | 2/2013 | Manwaring et al. | |
| 8,377,052 B2 | 2/2013 | Manwaring et al. | |
| 8,394,094 B2 | 3/2013 | Edwards et al. | |
| 8,425,503 B2 | 4/2013 | Manwaring et al. | |
| 8,491,578 B2 | 7/2013 | Manwaring et al. | |
| 8,491,626 B2 | 7/2013 | Roy et al. | |
| 8,523,850 B2 | 9/2013 | Manwaring et al. | |
| 8,523,852 B2 | 9/2013 | Manwaring et al. | |
| 8,551,088 B2 | 10/2013 | Falkenstein et al. | |
| 8,562,598 B2 | 10/2013 | Falkenstein et al. | |
| 8,568,411 B2 | 10/2013 | Falkenstein et al. | |
| 8,597,293 B2 | 12/2013 | Falkenstein et al. | |
| 8,597,297 B2 | 12/2013 | Couture et al. | |
| 8,617,151 B2 | 12/2013 | Denis et al. | |
| 8,623,003 B2 | 1/2014 | Lau et al. | |
| 8,636,730 B2 | 1/2014 | Keppel | |
| 8,734,445 B2 | 5/2014 | Johnson et al. | |
| 8,915,909 B2 | 12/2014 | Manwaring et al. | |
| 8,932,279 B2 | 1/2015 | Stringham et al. | |
| 8,951,248 B2 | 2/2015 | Messerly et al. | |
| 9,005,199 B2 | 4/2015 | Beckman et al. | |
| 9,039,694 B2 | 5/2015 | Ross et al. | |
| 9,050,100 B2 | 6/2015 | Yates et al. | |
| 9,084,606 B2 | 7/2015 | Greep | |
| 9,131,977 B2 | 9/2015 | Manwaring et al. | |
| 9,149,321 B2 | 10/2015 | Stringham et al. | |
| 9,192,427 B2 | 11/2015 | Johnson et al. | |
| 9,265,553 B2 | 2/2016 | Manwaring et al. | |
| 9,265,554 B2 | 2/2016 | Manwaring et al. | |
| 9,265,555 B2 | 2/2016 | Manwaring et al. | |
| 9,265,556 B2 | 2/2016 | Manwaring et al. | |
| 9,320,560 B2 | 4/2016 | Manwaring et al. | |
| 9,387,037 B2 | 7/2016 | Yang | |
| 9,402,679 B2 | 8/2016 | Ginnebaugh et al. | |
| 9,579,146 B2 | 2/2017 | Johnson et al. | |
| 9,918,774 B2 | 3/2018 | Batchelor et al. | |
| 9,931,157 B2 | 4/2018 | Strobl et al. | |
| 9,955,858 B2 | 5/2018 | Pamnani et al. | |
| 10,085,794 B2 | 10/2018 | Kerr et al. | |
| 10,204,773 B2 | 2/2019 | Sugiyama et al. | |
| 10,213,247 B2 | 2/2019 | Manwaring et al. | |
| 2007/0135808 A1 | 6/2007 | Kupferschmid et al. | |
| 2007/0265616 A1 | 11/2007 | Couture et al. | |
| 2008/0086195 A1 | 4/2008 | Atanasoka et al. | |
| 2012/0226270 A1 | 9/2012 | Manwaring et al. | |
| 2014/0135804 A1 | 5/2014 | Weisenburgh, II et al. | |
| 2014/0194875 A1 | 7/2014 | Reschke et al. | |
| 2016/0249975 A1 | 9/2016 | Konishi et al. | |
| 2016/0270810 A1* | 9/2016 | Vardi ............... A61B 17/32053 | |
| 2016/0278847 A1* | 9/2016 | Batchelor .......... A61B 18/1445 | |
| 2017/0156788 A1 | 6/2017 | Johnson et al. | |
| 2017/0196648 A1 | 7/2017 | Ward et al. | |
| 2018/0303322 A1 | 10/2018 | Pamnani et al. | |
| 2019/0000538 A1 | 1/2019 | Widenhouse et al. | |
| 2019/0053818 A1 | 2/2019 | Nelson et al. | |
| 2019/0262062 A1 | 8/2019 | Akagane | |

OTHER PUBLICATIONS

International Search Report and Written Opinion issued in corresponding International Application No. PCT/US2020/061998 mailed Mar. 22, 2021, 14 pages.

International Preliminary Report and Written Opinion issued in corresponding International Application No. PCT/US2020/061998 mailed Jun. 30, 2022, 7 pages.

ISR and Written Opinion PCT/US2021/053463 dated Oct. 20, 2020 7pp.

Invitation to Pay Additional Fees and Partial International Search Report received for PCT Patent Application No. PCT/US2021/051192, mailed on Dec. 23, 2021, 13 pages.

International Search Report and Written Opinion received for PCT Patent Application No. PCT/US2021/051192, mailed on Feb. 14, 2022, 18 pages.

* cited by examiner

THERMAL CUTTING ELEMENTS AND ELECTROSURGICAL INSTRUMENTS INCLUDING THERMAL CUTTING ELEMENTS

FIELD

The present disclosure relates to surgical instruments and, more particularly, to thermal cutting elements, and electrosurgical instruments including thermal cutting elements.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is an end effector for an electrosurgical instrument that includes a pair of opposing jaw members each having a jaw housing supporting an electrically conductive tissue engaging surface thereon. The electrically conductive tissue engaging surfaces are disposed in opposition relative to one another. One or both of the jaw members are movable relative to one another to grasp tissue therebetween. The electrically conductive tissue engaging surfaces are adapted to connect to an electrosurgical energy source.

A thermal cutting element is disposed in one or both of the electrically conductive tissue engaging surfaces, is independently activatable relative to the electrically conductive tissue engaging surfaces and is adapted to connect to the electrosurgical energy source. The thermal cutting element is exposed along the length of the electrically conductive tissue engaging surface and includes an exposed distal end extending through a distal end of the jaw housing. The thermal cutting element includes a scallop defined therein proximal to the exposed distal end thereof, the scallop is configured to facilitate scoring of tissue upon movement of the thermal cutting element relative to the tissue and upon activation thereof.

In aspects according to the present disclosure, the thermal cutting element includes an upper surface defined along a length thereof that is exposed to tissue when grasped between the opposing jaw members. In other aspects according to the present disclosure, the scallop is defined in the upper surface of the thermal cutting element.

In aspects according to the present disclosure, the thermal cutting element includes a cutting spine disposed along a length thereof having a pair of opposing beveled edges extending away therefrom that are configured to slough tissue away from the cutting spine once the tissue is cut. In other aspects according to the present disclosure, the scallop is defined in the cutting spine of the thermal cutting element.

In aspects according to the present disclosure, the thermal cutting element extends relative to a distal end of the jaw housing. In other aspects according to the present disclosure, the thermal cutting element includes chamfered edges at a distal end thereof. In yet other aspects according to the present disclosure, the thermal cutting element includes a chamfered edge disposed opposite the exposed upper surface thereof configured to reduce the profile of the thermal cutting element.

Provided in accordance with aspects of the present disclosure is an end effector for an electrosurgical instrument that includes a pair of opposing jaw members each having a jaw housing supporting an electrically conductive tissue engaging surface thereon. The electrically conductive tissue engaging surfaces are disposed in opposition relative to one another. One or both of the jaw members are movable relative to one another to grasp tissue therebetween. The electrically conductive tissue engaging surfaces are adapted to connect to an electrosurgical energy source.

A thermal cutting element is disposed in one or both of the electrically conductive tissue engaging surfaces, is independently activatable relative to the electrically conductive tissue engaging surfaces and is adapted to connect to the electrosurgical energy source. The thermal cutting element is exposed along the length of the electrically conductive tissue engaging surface and includes an exposed distal end extending through a distal end of the jaw housing. The thermal cutting element includes a scallop defined therein proximal to the exposed distal end thereof, the scallop is configured to facilitate scoring of tissue upon movement of the thermal cutting element relative to the tissue and upon activation thereof. A heating element is disposed within the scallop and is independently activatable relative to the thermal cutting element.

In aspects according to the present disclosure, one or more sensors are disposed within the scallop configured to monitor one or more parameters of the heating element. In other aspects according to the present disclosure, the one or more parameters includes power or temperature.

Provided in accordance with aspects of the present disclosure is an end effector for an electrosurgical instrument that includes a pair of opposing jaw members each having a jaw housing supporting an electrically conductive tissue engaging surface thereon. The electrically conductive tissue engaging surfaces are disposed in opposition relative to one another. One or both of the jaw members are movable relative to one another to grasp tissue therebetween. The electrically conductive tissue engaging surfaces are adapted to connect to an electrosurgical energy source.

A thermal cutting element is disposed in one or both of the electrically conductive tissue engaging surfaces, is independently activatable relative to the electrically conductive tissue engaging surfaces and is adapted to connect to the electrosurgical energy source. The thermal cutting element is exposed along the length of the electrically conductive tissue engaging surface and includes an exposed distal end extending through a distal end of the jaw housing. The thermal cutting element includes a scallop defined therein proximal to the exposed distal end thereof, the scallop is configured to facilitate scoring of tissue upon movement of the thermal cutting element relative to the tissue and upon activation thereof. A heating element is disposed within the scallop and is activatable with the thermal cutting element.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
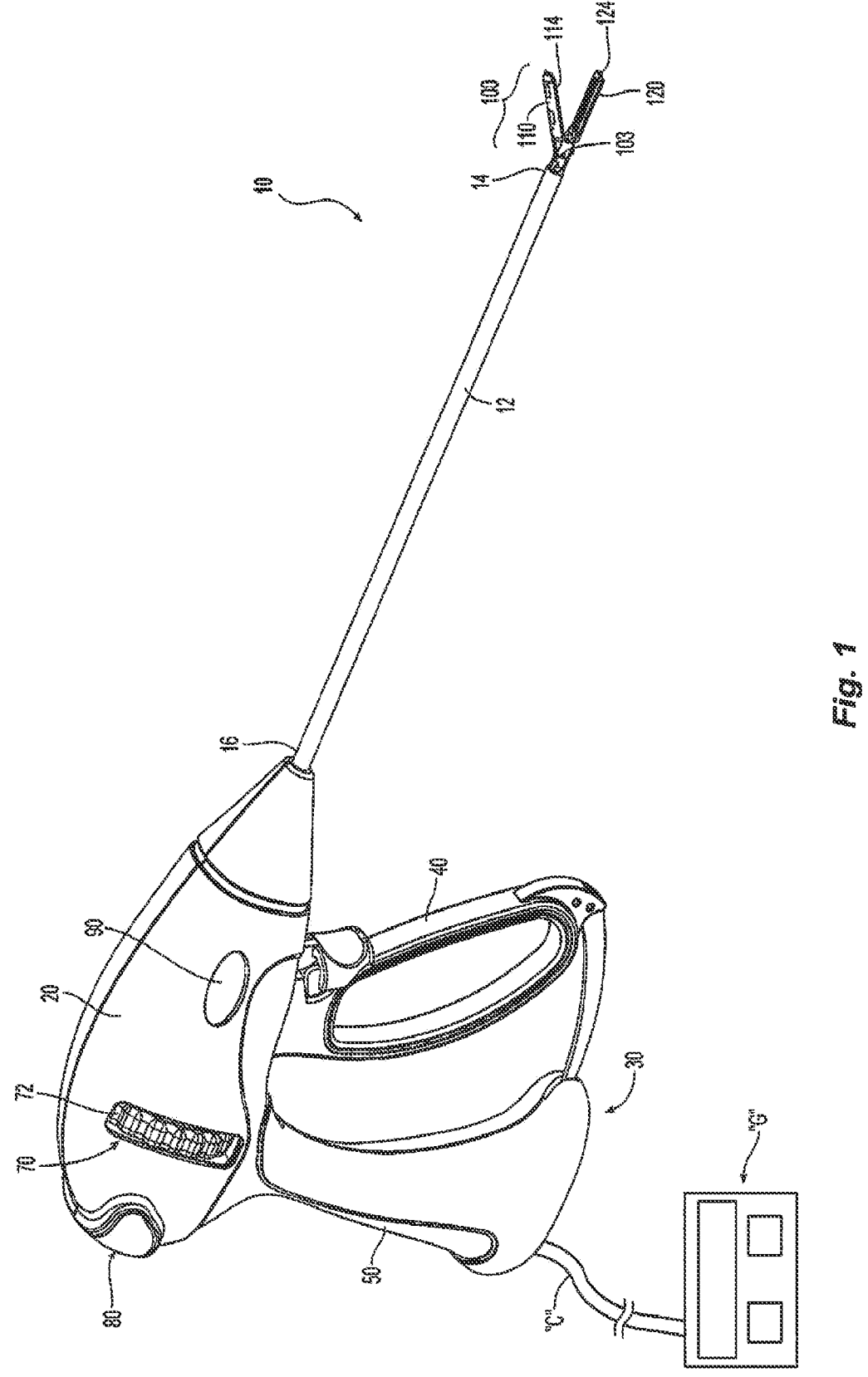
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, a first activation switch 80, a second activation switch 90, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue-treating surfaces 114, 124 of jaw members 110, 120, respectively, of end effector assembly 100 (see FIG. 4) to provide energy thereto. First activation switch 80 is coupled to tissue-treating surfaces 114, 124 (FIG. 4) and the electrosurgical generator "G" for enabling the selective activation of the supply of energy to jaw members 110, 120 for treating, e.g., cauterizing, coagulating/desiccating, and/or sealing, tissue. Second activation switch 90 is coupled to thermal cutting element 130 of jaw member 120 (FIG. 4) and the electrosurgical generator "G" for enabling the selective activation of the supply of energy to thermal cutting element 150 for thermally cutting tissue.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position and an approximated position to grasp tissue between tissue-treating surfaces 114, 124 of jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120. Rotating assembly 70 includes a rotation wheel 72 that is selectively rotatable in either direction to correspondingly rotate end effector assembly 100 relative to housing 20.

Figure 2:
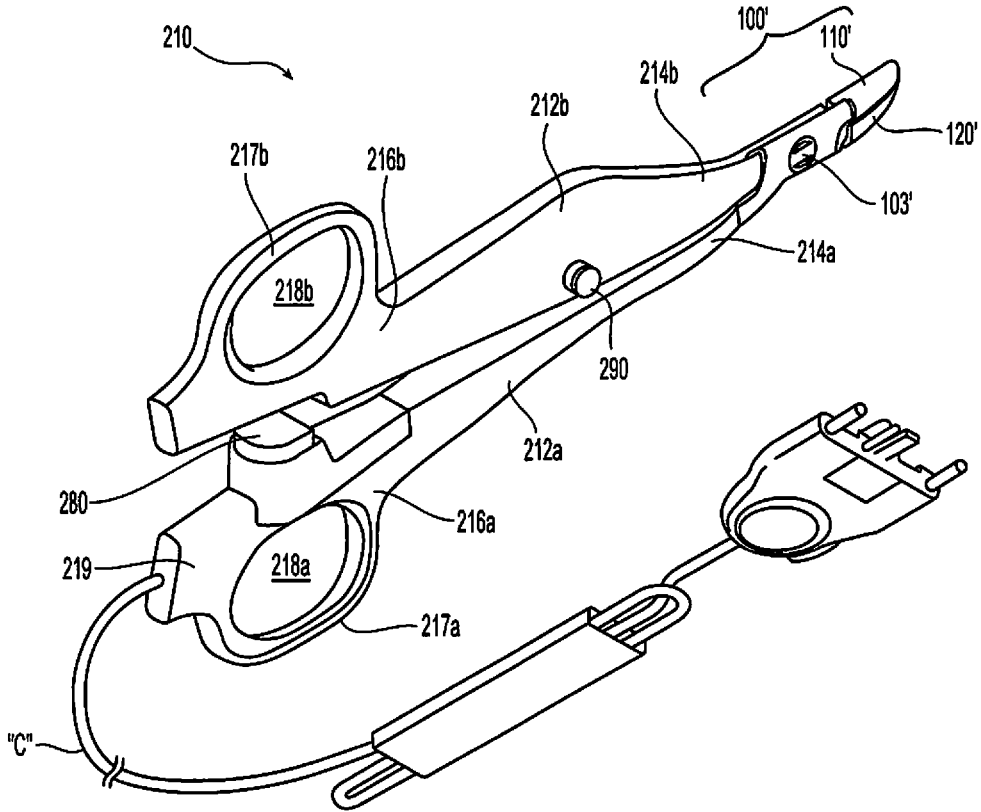
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Figure 4:
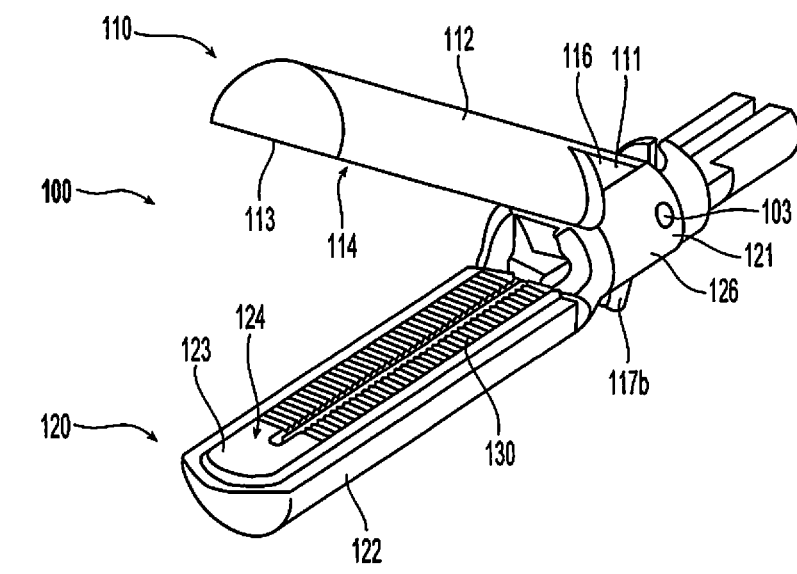
FIG. 4 is a perspective view of a distal end portion of the forceps of FIG. 1, wherein first and second jaw members of an end effector assembly of the forceps are disposed in a spaced-apart position.

Forceps 210 includes two elongated shaft members 212a, 212b, each having a proximal end portion 216a, 216b, and a distal end portion 214a, 214b, respectively. Forceps 210 is configured for use with an end effector assembly 100' similar to end effector assembly 100 (FIG. 4). More specifically, end effector assembly 100' includes first and second jaw members 110', 120' attached to respective distal end portions 214a, 214b of shaft members 212a, 212b. Jaw members 110', 120' are pivotably connected about a pivot 103'. Each shaft member 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212b, includes a proximal shaft connector 219 configured to connect forceps 210 to a source of energy, e.g., electrosurgical generator "G" (FIG. 1). Proximal shaft connector 219 secures a cable "C" to forceps 210 such that the user may selectively supply energy to jaw members 110', 120' for treating tissue. More specifically, a first activation switch 280 is provided for supplying energy to jaw members 110', 120' to treat tissue upon sufficient approximation of shaft members 212a, 212b, e.g., upon activation of first activation switch 280 via shaft member 212a. A second activation switch 290 disposed on either or both of shaft members 212a, 212b is coupled to the thermal cutting element (not shown, similar to thermal cutting element 150 of jaw member 120 (FIG. 4)) of one of the jaw members 110', 120' of end effector assembly 100' and to the electrosurgical generator "G" for enabling the selective activation of the supply of energy to the thermal cutting element for thermally cutting tissue.

Jaw members 110', 120' define a curved configuration wherein each jaw member is similarly curved laterally off of a longitudinal axis of end effector assembly 100'. However, other suitable curved configurations including curvature towards one of the jaw members 110, 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
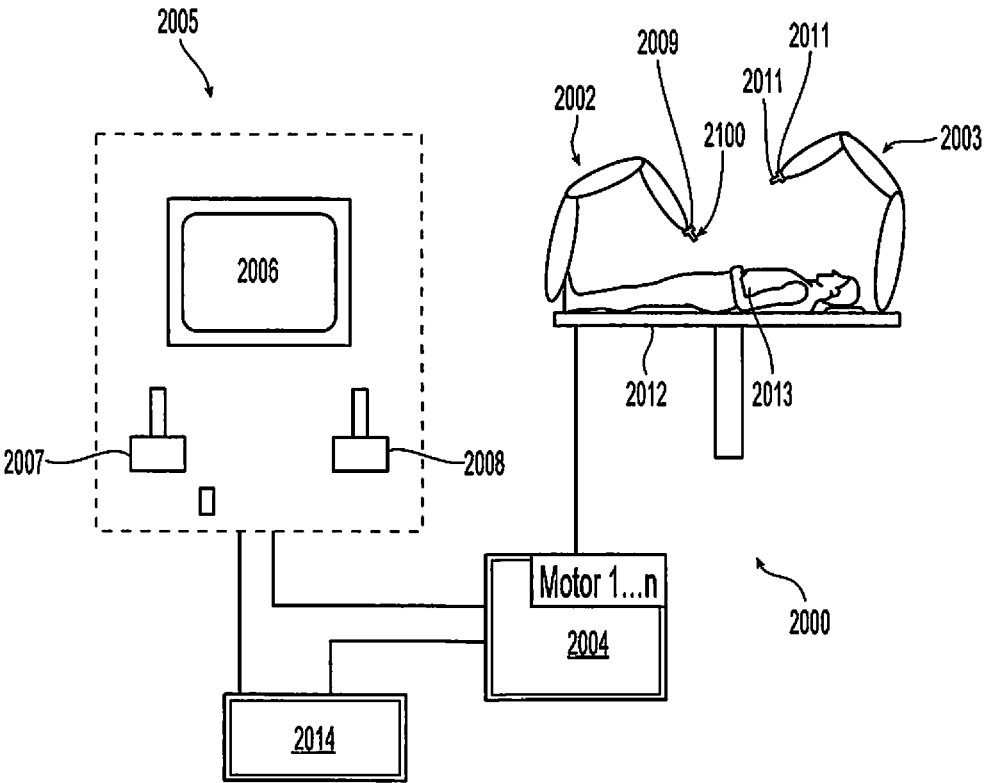
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 2000. Aspects and features of robotic surgical instrument 2000 not germane to the understanding of the present disclosure are omitted to avoid obscuring the aspects and features of the present disclosure in unnecessary detail.

Robotic surgical instrument 2000 includes a plurality of robot arms 2002, 2003; a control device 2004; and an operating console 2005 coupled with control device 2004. Operating console 2005 may include a display device 2006, which may be set up in particular to display three-dimensional images; and manual input devices 2007, 2008, by means of which a surgeon may be able to telemanipulate robot arms 2002, 2003 in a first operating mode. Robotic surgical instrument 2000 may be configured for use on a patient 2013 lying on a patient table 2012 to be treated in a minimally invasive manner. Robotic surgical instrument 2000 may further include a database 21014, in particular coupled to control device 2004, in which are stored, for example, pre-operative data from patient 2013 and/or anatomical atlases.

Each of the robot arms 2002, 2003 may include a plurality of members, which are connected through joints, and an attaching device 2009, 2011, to which may be attached, for example, an end effector assembly 2100, 2200, respectively. End effector assembly 2100 is similar to end effector assembly 100 (FIG. 4), although other suitable end effector assemblies for coupling to attaching device 2009 are also contemplated. End effector assembly 2200 may be any end effector assembly, e.g., an endoscopic camera, other surgical tool, etc. Robot arms 2002, 2003 and end effector assemblies 2100, 2200 may be driven by electric drives, e.g., motors, that are connected to control device 2004. Control device 2004 (e.g., a computer) may be configured to activate the motors, in particular by means of a computer program, in such a way that robot arms 2002, 2003, their attaching devices 2009, 2011, and end effector assemblies 2100, 2200 execute a desired movement and/or function according to a corresponding input from manual input devices 2007, 2008, respectively. Control device 2004 may also be configured in such a way that it regulates the movement of robot arms 2002, 2003 and/or of the motors.

Turning to FIG. 4, one embodiment of a known end effector assembly 100, as noted above, includes first and second jaw members 110, 120. Each jaw member 110, 120 may include a structural frame 111, 121, a jaw housing 112, 122, and a tissue-treating plate 113, 123 defining the respective tissue-treating surface 114, 124 thereof. Alternatively, only one of the jaw members, e.g., jaw member 120, may include the structural frame 121, jaw housing 122, and tissue-treating plate 123 defining the tissue-treating surface 124. In such embodiments, the other jaw member, e.g., jaw member 110, may be formed as a single unitary body, e.g., a piece of conductive material acting as the structural frame 111 and jaw housing 112 and defining the tissue-treating surface 114. An outer surface of the jaw housing 112, in such embodiments, may be at least partially coated with an insulative material or may remain exposed. In embodiments, tissue-treating plates 113, 123 may be deposited onto jaw housings 112, 122 or jaw inserts (not shown) disposed within jaw housings 112, 122, e.g., via sputtering. Alternatively, tissue-treating plates 113, 123 may be pre-formed and engaged with jaw housings 112, 122 and/or jaw inserts (not shown) disposed within jaw housings 112, 122 via, for example, overmolding, adhesion, mechanical engagement, etc.

Figure 5A:
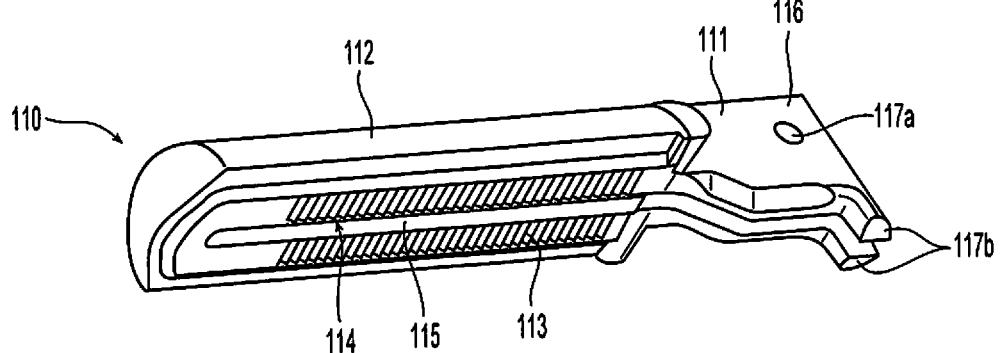
FIG. 5A is a bottom, perspective view of the first jaw member of the end effector assembly of FIG. 4.
Figure 5B:
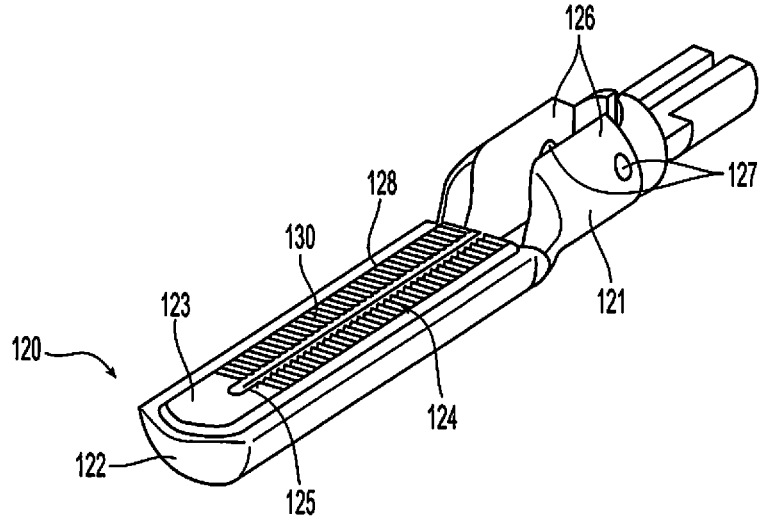
FIG. 5B is a top, perspective view of the second jaw member of the end effector assembly of FIG. 4.

Referring in particular to FIGS. 4-5B, jaw member 110, as noted above, may be configured similarly as jaw member 120, may be formed as a single unitary body, or may be formed in any other suitable manner so as to define a structural frame 111 and a tissue-treating surface 114 opposing tissue-treating surface 124 of jaw member 120. Structural frame 111 includes a proximal flange portion 116 about which jaw member 110 is pivotably coupled to jaw member 120. In shaft-based or robotic embodiments, proximal flange portion 116 may further include an aperture 117a for receipt of pivot 103 and at least one protrusion 117b extending therefrom that is configured for receipt within an aperture defined within a drive sleeve of the drive assembly (not shown) such that translation of the drive sleeve, e.g., in response to actuation of movable handle 40 (FIG. 1) or a robotic drive, pivots jaw member 110 about pivot 103 and relative to jaw member 120 between the spaced-apart position and the approximated position. However, other suitable drive arrangements are also contemplated, e.g., using cam pins and cam slots, a screw-drive mechanism, etc.

Regardless of the particular configuration of jaw member 110, jaw member 110 may include a longitudinally-extending insulative member 115 extending along at least a portion of the length of tissue-treating surface 114. Insulative member 115 may be transversely centered on tissue-treating surface 114 or may be offset relative thereto. Further, insulative member 115 may be disposed, e.g., deposited, coated, etc., on tissue-treating surface 114, may be positioned within a channel or recess defined within tissue-treating surface 114, or may define any other suitable configuration. Additionally, insulative member 115 may be substantially (within manufacturing, material, and/or use tolerances) coplanar with tissue-treating surface 114, may protrude from tissue-treating surface 114, may be recessed relative to tissue-treating surface 114, or may include different portions that are coplanar, protruding, and/or recessed relative to tissue-treating surface 114. Insulative member 115 may be formed from, for example, ceramic, parylene, nylon, PTFE, or other suitable material(s) (including combinations of insulative and non-insulative materials).

With reference to FIGS. 4 and 5B, as noted above, jaw member 120 includes a structural frame 121, a jaw housing 122, and a tissue-treating plate 123 defining the tissue-treating surface 124 thereof. Jaw member 120 further include a thermal cutting element 130. Structural frame 121 defines a proximal flange portion 126 and a distal body portion (not shown) extending distally from proximal flange portion 126. Proximal flange portion 126 is bifurcated to define a pair of spaced-apart proximal flange portion segments that receive proximal flange 111 of jaw member 110 therebetween and define aligned apertures 127 configured for receipt of pivot 103 therethrough to pivotably couple jaw members 110, 120 with one another.

Jaw housing 122 of jaw member 120 is disposed about the distal body portion of structural frame 121, e.g., via overmolding, adhesion, mechanical engagement, etc., and supports tissue-treating plate 123 thereon, e.g., via overmolding, adhesion, mechanical engagement, depositing (such as, for example, via sputtering), etc. Tissue-treating plate 123, as noted above, defines tissue-treating surface 124. A longitudinally-extending slot 125 is defined through tissue-treating plate 123 and is positioned to oppose insulative member 115 of jaw member 110 (FIG. 5A) in the approximated position. Slot 125 may extending through at least a portion of jaw housing 122, a jaw insert (if so provided), and/or other components of jaw member 120 to enable receipt of thermal cutting element 130 at least partially within slot 125.

Thermal cutting element 130, more specifically, is disposed within longitudinally-extending slot 125 such that thermal cutting element 130 opposes insulative member 115 of jaw member 110 (FIG. 5A) in the approximated position. Thermal cutting element 130 may be configured to contact insulative member 115 (FIG. 5A) in the approximated position to regulate or contribute to regulation of a gap distance between tissue-treating surfaces 114, 124 in the approximated position. Alternatively or additionally, one or more stop members (not shown) associated with jaw member 110 and/or jaw member 120 may be provided to regulate the gap distance between tissue-treating surfaces 114, 124 in the approximated position.

Thermal cutting element 130 may be surrounded by an insulative member 128 disposed within slot 125 to electrically isolate thermal cutting element from tissue-treating plate 123. Alternatively or additionally, thermal cutting element 130 may include an insulative coating on at least the sides thereof for similar purposes. Thermal cutting element 130 and insulative member 128 may similarly or differently be substantially (within manufacturing, material, and/or use tolerances) coplanar with tissue-treating surface 124, may protrude from tissue-treating surface 124, may be recessed relative to tissue-treating surface 124, or may include different portions that are coplanar, protruding, and/or recessed relative to tissue-treating surface 124.

In embodiments where end effector assembly 100, or a portion thereof, is curved, longitudinally-extending slot 125 and thermal cutting element 130 may similarly be curved, e.g., wherein longitudinally-extending slot 125 and thermal cutting element 130 (or corresponding portions thereof) are relatively configured with reference to an arc (or arcs) of curvature rather than a longitudinal axis. Thus, the terms longitudinal, transverse, and the like as utilized herein are not limited to linear configurations, e.g., along linear axes, but apply equally to curved configurations, e.g., along arcs of curvature. In such curved configurations, insulating member 115 of jaw member 110 (FIG. 5A) is likewise curved.

Generally referring to FIGS. 1-5B, tissue-treating plates 113, 123 are formed from an electrically conductive material, e.g., for conducting electrical energy therebetween for treating tissue, although tissue-treating plates 113, 123 may alternatively be configured to conduct any suitable energy, e.g., thermal, microwave, light, ultrasonic, etc., through tissue grasped therebetween for energy-based tissue treatment. As mentioned above, tissue-treating plates 113, 123 are coupled to activation switch 80 and electrosurgical generator "G" (FIG. 1) such that energy may be selectively supplied to tissue-treating plates 113, 123 and conducted therebetween and through tissue disposed between jaw members 110, 120 to treat tissue, e.g., seal tissue on either side and extending across thermal cutting element 130.

Thermal cutting element 130, on the other hand, is configured to connect to electrosurgical generator "G" (FIG. 1) and second activation switch 90 to enable selective activation of the supply of energy to thermal cutting element 130 for heating thermal cutting element 130 to thermally cut tissue disposed between jaw members 110, 120, e.g., to cut the sealed tissue into first and second sealed tissue portions. Other configurations including multi-mode switches, other separate switches, etc. may alternatively be provided. Cross reference is made to U.S. Provisional Patent Application Ser. No. 62/952,232 the entire contents of which being incorporated by reference herein.

Figure 6:
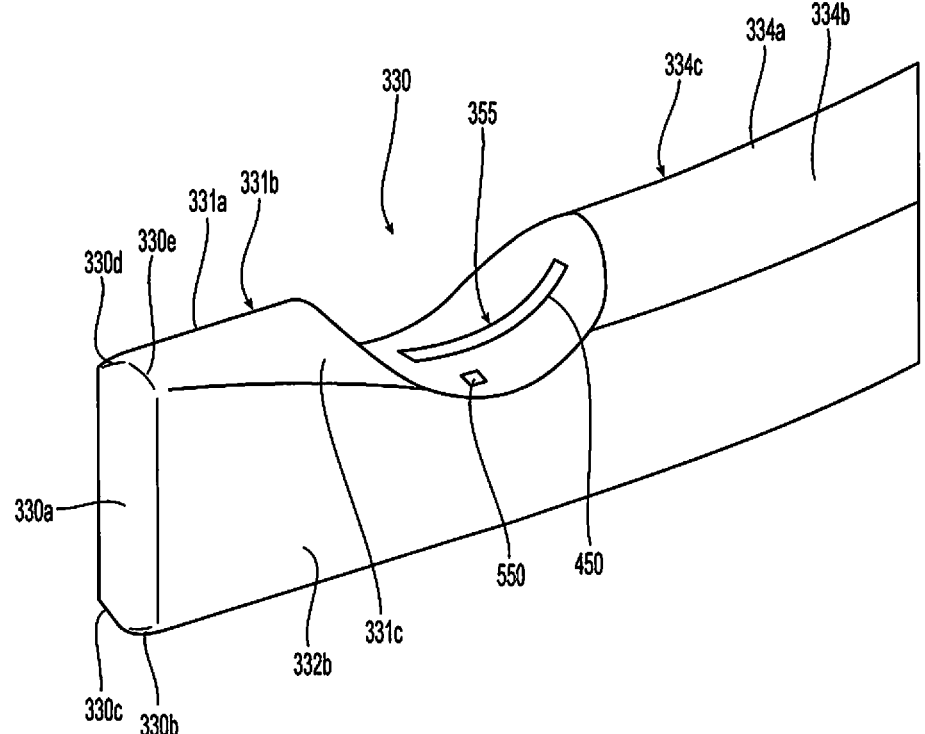
FIG. 6 is an enlarged, front perspective view of a distal end of a thermal cutting element according to the present disclosure.

Referring to FIG. 6, an alternate embodiment of a thermal cutting element 330 is shown that includes geometry to facilitate cutting and sloughing of tissue post cutting. For example, upper exposed edge of the distal end 330 of the thermal cutting element 330 includes a cutting spine 331*a* having a pair of opposing beveled edges 331*b*, 331*c* extending away therefrom that are configured to slough tissue away from the cutting spine 331*a* once cut. In addition, the exposed end 330*a* of the thermal cutting element 330 is chamfered or rounded to form exposed ends 330*b*-330*e*. Reducing the sharp edges at the distal end 330*a* of the thermal cutting element 330 reduces unintended tissue trauma while electrically cutting tissue. Likewise, other exposed edges, e.g., side edges and bottom edge, may be beveled, chamfered or rounded as well depending upon a particular purpose. Configuring the thermal cutting element 330 to be exposed at a distal end 330*a* thereof facilitates dissection, back-scoring of tissue and/or facilitates the creation of an enterotomy.

Thermal cutting element 330 also includes other areas configured to reduce sharp edges along the length thereof, e.g., chamfered edges 332*b* (opposite side not shown) proximate the distal end 330*a* of the thermal cutting element 330 and extending proximally therefrom. Edge 332*b* and opposite edge (not shown) are configured to reduce the profile of the thermal cutting element 330 extending proximally from distal end 330*a* and may also facilitate tissue separation when the thermal cutting element 330 is moved distally through tissue. Other geometries of the thermal cutting element 330 are configured to further enhance the cutting process, e.g., spine 334*a* with opposing beveled edges 334*b*, 334*c*.

Thermal cutting element 330 also includes a back scallop 355 defined therein proximate the distal end 330*a* thereof. Back scallop 355 is disposed along an upper surface of thermal cutting element 330 between spines 331*a* and 334*a*. Back scallop 355 is configured to facilitate scoring of tissue when the upper surface of the thermal cutting element 330 is moved along tissue. For example, tissue may be placed atop the thermal cutting element 330 and then the thermal cutting element 330 may be moved proximally to back score the tissue. The process may be repeated to divide tissue in this same fashion. The geometry of the back scallop 355 may be dimensioned to maximize tissue scoring during a single stroke or provide minimal scoring during a single stroke depending upon a particular purpose. Moreover, the geometry of the scallop, e.g., "J-like", may be dimensioned to facilitate handling tissue.

A separate heating element 450 may be disposed within the back scallop 355 and activated independently (or sequentially or simultaneously) of the thermal cutting element 330 depending upon a particular purpose. In this instance, the separate heating element 450 would be encased in an insulative material (not shown) to allow selective activation thereof. One or more sensors 550 may be utilized to monitor the separate heating element 450 or the back scallop 355, e.g., power, temperature, etc. from of the scallop 335, during activation of either the separate heating element 450 or activation of the thermal cutting element 330.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for an electrosurgical instrument, comprising:

a pair of opposing jaw members each including a jaw housing supporting an electrically conductive tissue engaging surface thereon, the electrically conductive tissue engaging surfaces disposed in opposition relative to one another, at least one of the pair of jaw members movable relative to the other of the pair of jaw members to grasp tissue therebetween, the electrically conductive tissue engaging surfaces adapted to connect to an electrosurgical energy source;

a thermal cutting element disposed in at least one of the electrically conductive tissue engaging surfaces, the thermal cutting element independently activatable relative to the electrically conductive tissue engaging surfaces and adapted to connect to the electrosurgical energy source, the thermal cutting element exposed along the length of the at least one electrically conductive tissue engaging surface and including an exposed distal end extending through a distal end of the jaw housing, the thermal cutting element including a scallop defined therein proximal to the exposed distal end thereof, the scallop configured to facilitate scoring of tissue upon movement of the thermal cutting element relative to tissue and upon activation thereof;

a heating element located within the scallop; and at least one sensor located within the scallop configured to monitor at least one parameter of the heating element.

2. The end effector assembly according to claim 1, wherein the thermal cutting element includes an upper surface defined along a length thereof that is exposed to tissue when grasped between the opposing jaw members.

3. The end effector assembly according to claim 2, wherein the scallop is defined in the upper surface of the thermal cutting element.

4. The end effector assembly according to claim 2, wherein the thermal cutting element includes a chamfered edge disposed opposite the exposed upper surface thereof configured to reduce a profile of the thermal cutting element.

5. The end effector assembly according to claim 1, wherein the thermal cutting element includes a cutting spine disposed along a length thereof having a pair of opposing beveled edges extending away therefrom that are configured to slough tissue away from the cutting spine once the tissue is cut.

6. The end effector assembly according to claim 5, wherein the scallop is defined in the cutting spine of the thermal cutting element.

7. The end effector assembly according to claim 1, wherein the thermal cutting element extends relative to a distal end of the jaw housing.

8. The end effector assembly according to claim 1, wherein the thermal cutting element includes chamfered edges at a distal end thereof.

9. The end effector assembly according to claim 1, wherein the thermal cutting element includes a spine at an upper exposed edge of a distal end of the thermal cutting element and another spine at the upper exposed edge proximal the scallop.

10. The end effector assembly according to claim 1, wherein the heating element is encased in an insulative material.

11. The end effector assembly according to claim 1, wherein the at least one parameter of the heating element includes power or temperature.

12. An end effector assembly for an electrosurgical instrument, comprising:

a pair of opposing jaw members each including a jaw housing supporting an electrically conductive tissue engaging surface thereon, the electrically conductive tissue engaging surfaces disposed in opposition relative to one another, at least one of the pair of jaw members movable relative to the other of the pair of jaw members to grasp tissue therebetween, the electrically conductive tissue engaging surfaces adapted to connect to an electrosurgical energy source;

a thermal cutting element disposed in at least one of the electrically conductive tissue engaging surfaces, the thermal cutting element independently activatable relative to the electrically conductive tissue engaging surfaces and adapted to connect to the electrosurgical energy source, the thermal cutting element exposed along the length of the at least one electrically conductive tissue engaging surface and including an exposed distal end extending through a distal end of the jaw housing, the thermal cutting element including a scallop defined therein proximal to the exposed distal end thereof, the scallop configured to facilitate scoring of tissue upon movement of the thermal cutting element relative to tissue and upon activation thereof;

a heating element disposed within the scallop, the heating element independently activatable relative to the thermal cutting element; and at least one sensor located within the scallop configured to monitor at least one parameter of the heating element.

13. The end effector assembly according to claim 12, wherein the at least one parameter of the heating element includes power or temperature.

14. The end effector assembly according to claim 12, wherein the thermal cutting element includes a spine at an upper exposed edge of a distal end of the thermal cutting element and another spine at the upper exposed edge proximal the scallop.

15. The end effector assembly according to claim 12, wherein the heating element is encased in an insulative material.

16. An end effector assembly for an electrosurgical instrument, comprising:

a pair of opposing jaw members each including a jaw housing supporting an electrically conductive tissue engaging surface thereon, the electrically conductive tissue engaging surfaces disposed in opposition relative to one another, at least one of the pair of jaw members movable relative to the other of the pair of jaw members to grasp tissue therebetween, the electrically conductive tissue engaging surfaces adapted to connect to an electrosurgical energy source;

a thermal cutting element disposed in at least one of the electrically conductive tissue engaging surfaces, the thermal cutting element independently activatable relative to the electrically conductive tissue engaging surfaces and adapted to connect to the electrosurgical energy source, the thermal cutting element exposed along the length of the at least one electrically conductive tissue engaging surface and including an exposed distal end extending through a distal end of the jaw housing, the thermal cutting element including a scal-
lop defined therein proximal to the exposed distal end
thereof, the scallop configured to facilitate scoring of
tissue upon movement of the thermal cutting element
relative to tissue and upon activation thereof;

a heating element disposed within the scallop, the heating
element activatable with the thermal cutting element;
and at least one sensor located within the scallop configured to
monitor at least one parameter of the heating element.

17. The end effector assembly according to claim 16,
wherein the thermal cutting element includes a spine at an
upper exposed edge of a distal end of the thermal cutting
element and another spine at the upper exposed edge proxi-
mal the scallop.

18. The end effector assembly according to claim 16,
wherein the at least one parameter of the heating element
includes power or temperature.

\* \* \* \* \*